United States Patent [19]

Fraser

[11] 4,267,841

[45] May 19, 1981

[54] NAIL MATRIX TREPHINE

[76] Inventor: Alexander R. Fraser, 2 Ralston Pl., West Ferry, Dundee, Scotland

[21] Appl. No.: 972,635

[22] Filed: Dec. 22, 1978

[30] Foreign Application Priority Data

Jan. 6, 1978 [GB] United Kingdom ............... 562/78

[51] Int. Cl.³ .................. A61F 17/32; A61B 17/00; A61F 5/04
[52] U.S. Cl. ................ 128/305; 128/305.1; 128/92 EB; 128/346
[58] Field of Search ............... 128/305, 305.1, 92 EB, 128/346

[56] References Cited

U.S. PATENT DOCUMENTS

| Re. 27,032 | 1/1971 | Hall | 128/305.1 |
|---|---|---|---|
| 983,368 | 2/1911 | Holt | 128/305.1 |
| 2,181,746 | 11/1939 | Siebrandt | 128/305.1 |
| 3,628,522 | 12/1971 | Kato | 128/305.1 |
| 3,727,611 | 4/1973 | Schultz | 128/92 EB |
| 3,945,377 | 3/1976 | Kronner | 128/92 EB |
| 3,989,033 | 11/1976 | Halpern et al. | 128/305 |
| 4,058,126 | 11/1977 | Leveen | 128/305 |
| 4,111,208 | 9/1978 | Leuenberg | 128/305.1 |

FOREIGN PATENT DOCUMENTS 910078 of 1946 France ...................... 128/92 EB

*Primary Examiner*—Robert W. Michell
*Assistant Examiner*—C. W. Shedd
*Attorney, Agent, or Firm*—Ladas & Parry

[57] ABSTRACT

A nail matrix trephine includes clamping head for clamping the trephine to a nail plate and a guide head for guiding a trephine cutter. The clamping head and guide head are interconnected by means of an adjustment device so that when the clamping head is clamped to the nail plate the guide head is adjusted relative thereto so that the trephine cutter is guided to remove preselected nail matrix cells.

6 Claims, 4 Drawing Figures

NAIL MATRIX TREPHINE

BACKGROUND OF THE INVENTION

This invention relates to a nail-matrix trephine which is to be used in a surgical operation for selecting and effecting the eradication of unwanted nail-matrix cells.

In order to understand the need for such operations it must be stated that a reduction in the breadth of a nail plate can often relieve undue pressure that occurs in nail grooves of people who are having to contend with unnatural walking conditions and footwear.

Some of the existing techniques concerned with the partial eradication of nail-matrix tissue have not been successful and total eradication has been resorted to by some surgeons. The latter operations have also proved to have their limitations. The problem is the difficulty in ensuring that all germinating cells are removed and that no regeneration of these cells takes place. Some techniques resorted to appear to be unnecessarily radical and often result, even in partial resections, in damage to the eponychium and nail bed distal to the lunula region. In total and partial resections it is common to have a displacement of germinating cells resulting in fragments of nail development, the appearance of which may be months after the operation.

As indicated above the history of such operations shows that there are problems in effecting the clean removal of unwanted nail-matrix germinating cells. Consequently, the endeavours to achieve a clean field has resulted in more radical operations, involving the removal of tissue which does not germinate nail cells.

An appreciation of existing surgical instruments and techniques can be gained by studying the section dealing with nail conditions in the book, 'Surgery of the Foot' by Henry L. DuVries, published by C. V. Mosly Company of Saint Louis, U.S.A.

SUMMARY OF THE INVENTION

According to the present invention there is provided a nail-matrix trephine adapted to be attached to a nail plate of a toe or finger for removing unwanted nail-matrix cells, including a clamping head comprising a hooked nail engaging member adapted to be located beneath a nail plate, a clamping member mounted on said clamping head and adapted to co-operate with said hooked nail engaging member to firmly attach said clamping head to said nail plate and clamp alignment means on said hooked nail engaging member for aligning said clamping head on said nail plate, a guide head adapted for supporting and guiding trephine cutter means mounted thereon, and adjustable means interconnecting said clamping head and said guide head and adapted to adjust one said head relative to the other said head, wherein upon clamping and aligning said clamping head to said nail plate the position of said guide head is adjusted so that when said trephine cutter means is advanced a selected portion of the nail-matrix cells is removed.

Preferably, said adjustable means includes guide rails on which said clamping head and said guide head are movable one relative to the other. Conveniently, adjustable means comprises a screw for moving said clamping head and guide head one relative to the other.

In a preferred embodiment of a nail-matrix trephine according to the invention the clamping member on the clamping head comprises a screw while the alignment means on the hooked nail engaging member comprises a surface of said member. Preferably, the trephine cutter means comprises a screw movable in said guide head and having a cutting surface at one end thereof.

The employment of a controlled trephine confines the surgery, in the partial resection of the nail-matrix sheath, to an immediate or restricted location, thus avoiding unnecessary damage to other tissues and yet providing ample scope to ensure a complete clearance of germinating cells. It is expected that the patient will be able to walk in comfort immediately after an operation in which the nail matrix trephine is utilised.

BRIEF DESCRIPTION OF DRAWINGS

An embodiment of the present invention will now be described by way of example with reference to the accompanying drawings, in which.

DESCRIPTION OF PREFERRED EMBODIMENT

Figure 1:
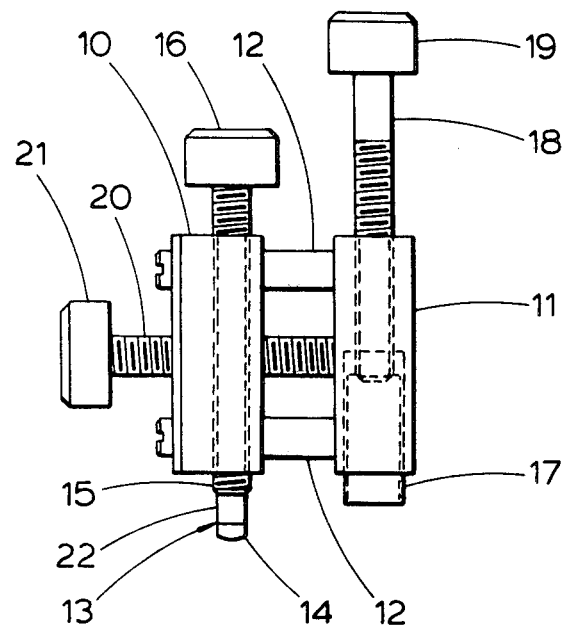
FIG. 1 is a plan view of a nail-matrix trephine according to the present invention.
Figure 2:
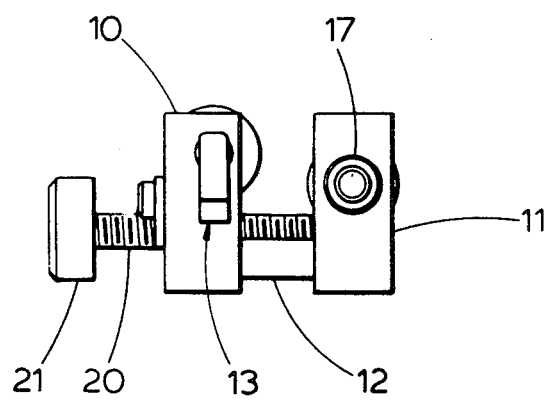
FIG. 2 is an end elevational view towards the trephine cutter of the nail-matrix trephine of FIG. 1.
Figure 3:
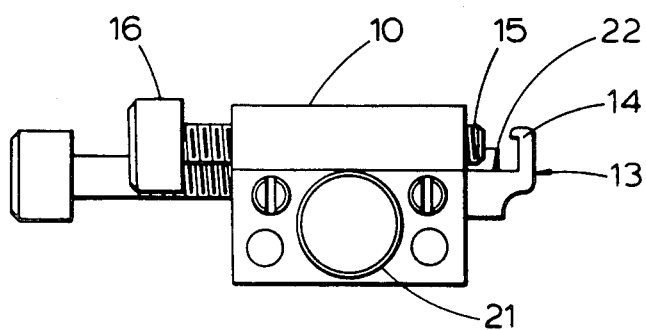
FIG. 3 is a side elevational view of the nail-matrix trephine of FIG. 1.

Referring now particularly to FIGS. 1 to 3 of the drawings there is shown a nail-matrix trephine having a clamping portion 10 and a trephine cutter portion 11 interconnected for relative movement therebetween by guide rails 12. The clamping portion 10 has a fixed hook 13 which extends outwardly from the clamping portion in a direction perpendicular to the longitudinal axis of the guide rails 12. The free curved end 14 of the hook projects into the path of a clamping screw 15 which extends through the body of the clamping portion and is provided at its opposite end with a knurled head 16 to enable the screw to be moved towards or away from the free end of the hook.

The trephine cutter portion 11 is provided with a trephine cutter 17 which is coupled to a screw 18 having a knurled head 19, and projects from the side of the trephine cutter portion opposite to that from which the trephine cutter projects. Movement of the screw 18 causes inward and outward movement of the trephine cutter 17.

The guide rails 12 are fixed to the clamping portion 10 so that upon adjustment of a screw 20, having a knurled head 21, the trephine cutter portion 11 can be moved towards or away from the clamping portion. Such movement between the clamping and cutter portions advantageously allows for the precise location of the trephine cutter.

The nail-matrix trephine described above may be made from any one of a number of metals suitably selected to meet the standards of surgical instruments.

In the operation of the nail-matrix trephine the clamp portion 10 is positioned distally from the region of the unwanted nail-matrix cells in the region of the exposed nail surface to enable its securing components 14 and 15 to be clamped to the relevant side or lateral edge of a nail plate. The trephine cutter portion 11 is positioned proximally to the region of the unwanted nail-matrix cells so that its trephine cutter 17 is suitably positioned to bore through the skin, subcutaneous tissue and nail tissue, when the trephine is operated.

Figure 4:
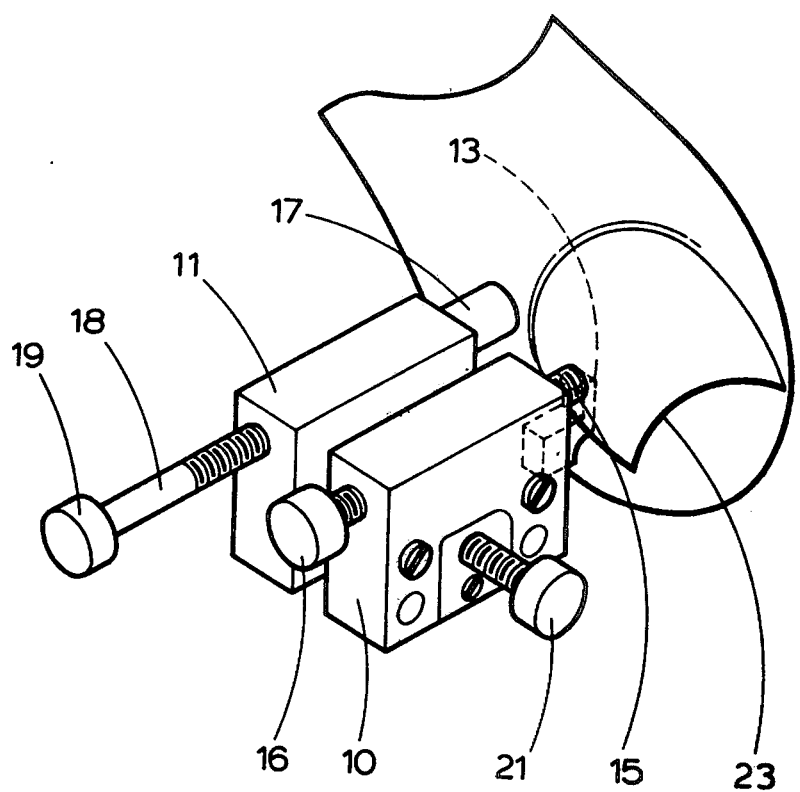
FIG. 4 is a perspective view of the nail-matrix trephine of FIG. 1 in use on a toe nail.

The hook part 14 and screw 15 forming the clamping components are ideally placed as far as possible from the free edge 23 of the nail, as indicated on FIG. 4. The nearer this clamping, on the exposed part of the nail, is to the concealed part of the matrix on which the operation is to be carried out, the better the results should be. In a healthy nail it would not be possible to fit the clamping section without creating lysis. The fact that lysis exists along the borders of troublesome nails is often due to the close proximity that the lateral nail folds have with the nail plate in the wearers of enclosed footwear. These lateral lips of tissue interfere with the passage of water vapour through the nail plate and the resultant excess of subungual fluid causes lysis. This lysis leads to further pathological changes such as dehydration of the nail plate, nail-curvature and the formation of callous tissue in the nail groove. In some cases a liberal lip of lateral fold will be judged to be a predominant cause of the patient's discomfort. In many cases a wedge resection of this lip of tissue will obviate the need for the partial resection of the nail-matrix sheath.

If good attachment exists between the nail plate and the nail bed it is still quite easy, under anaesthesia, to fit the securing clamp to the nail edge. The hook only extends 3 mm under the nail.

When pathological changes lead to mal-curvature of the nail the lateral edge of the nail will converge on the midline of the nail. This convergence becomes more accentuated towards the free edge 23 of the nail. It is for this reason that the clamp should be pushed into the most proximal position to the unwanted nail matrix cells on the exposed lateral edge. The nail there will closely resemble, in form, the shape being produced in the nail-matrix sheath. This means, in effect, that the nearer the clamp is to the operating position of the trephine the more accurate the longitudinal alignment should be. The trephine is set so that its cutting edge should come approximately 2.5 mm over the lateral edge of the nail in the matrix, the trephine bore being 5 mm in diameter.

When hook 13 is postioned under the lateral edge of the nail, as discussed above, screw 15 is screwed down to bear on the nail plate disposed between the hook and the screw, and the hook will be brought into a tight relationship with the undersurface of the nail plate. Care must be exercised to ensure that the flat surface 22 of the hook 13 lies in as good a contact as possible with the lateral border of the nail because this sets the instrument in alignment with the lateral edge of the nail and the corresponding edge of the concealed matrix. The instrument setting will also be influenced by the transverse and longitudinal planes of the nail plate on which it is seated. Its vertical plane will extend at an angle of approximately 90° to the point of attachment. Congruous with this setting the trephine will be poised at an angle of approximately 90° to the concealed unwanted part of the nail matrix.

Final selection of the longitudinal position of the trephine relative to the clamping portion 10 may be necessary and this can be effected by the lateral adjusting screw 20 which can bring portions 10 and 11 together or separate them as required.

At this stage the trephine cutter 17 will be set in a high position so that it is clear of the skin. When the location for the operation is established, the trephine will be screwed into the tissue. When its cutting edge has reached the unwanted matrix nail cells its position will correspond approximately to the level of the exposed surface of the nail where the clamping portion 10 is secured. This position may be calibrated as a guide. The tissue will, however, offer increased resistance to the cutter and this, together with the decrease in resistance when the section of nail has been severed, will enable the operator to judge that the boring operation is complete. The boring operation should continue until bone resistance is felt to help ensure that the inferior part of the matrix sheath is detached from adjacent tissue. The trephine then is unscrewed and the clamping portion removed.

The lateral adjusting screw 20 will give a range of movement which is more than ample. The nail-matrix sheath has a distal line congruous with the distal line of the toe. The degree of curvature varies considerably but it is contended that, even allowing for different curves, the proximal corners of the matrix occupy a similar position.

Indeed, as a general guide one need only take a transverse line from the mid-point of the eponychium to give a position that will include the distal line of the matrix.

If there is a prominent lunula the trephine could with advantage be positioned just in front of this line depending on how much of the nail-matrix is to be removed. One can also ascertain the position of the proximal and lateral margins of the matrix by testing the anaesthetised area with a fine needle. The needle can be tested for depth over the matrix and then the border of the matrix established by deeper penetration. A line can be drawn giving ones estimation of the margin of the matrix.

When the area has been selected a skin marking may be made to assist the correct replacement of the skin tissue.

The simple operation of the technique described above is dependent upon the positioning of the trephine because an opening is created for the insertion of mousetoothed Spencer-Well's forceps to extract the core of tissue. Equally important, accurate positioning ensures that a substantial portion of the lateral edge is removed, particularly with the cutting-head having a diameter of 5 mm. A nail matrix can have a depth of 5 mm and indeed greater than this is the mid-point of a very curved matrix. It is believed that there is little advantage in providing a cutting head much bigger than 5 mm because the final reshaping of the matrix will be done with tissue nippers and there should be ample scope to effect this with the 5 mm aperture. However, the cutting head may have a diameter which is greater or smaller than 5 mm.

It will be appreciated that right side and left side versions of the nail matrix trephine are available for operations on both the right and left sides of a nail.

What is claimed is:

1. A nail-matrix trephine adapted to be attached to a nail plate of a toe or finger for removing unwanted nail-matrix cells, including a clamping head comprising a hooked nail engaging member adapted to be located beneath a nail plate, a clamping member mounted on said clamping head and adapted to co-operate with said hooked nail engaging member to firmly attach said clamping head to said nail plate and clamp alignment means on said hooked nail engaging member for aligning said clamping head on said nail plate, a guide head adapted for supporting and guiding trephine cutter means mounted thereon, and adjustable means interconnecting said clamping head and said guide head, wherein the adjustable means includes guide rails on which said clamping head and said guide head are moveable one relative to the other and further including a screw for moving said heads one relative to the other; wherein upon clamping and aligning said clamping head to said nail plate the position of said guide head is adjusted so that when said trephine cutter means is advanced a selected portion of the nail-matrix cells is removed.

2. A nail matrix trephine as claimed in claim 1, wherein said clamping member comprises a screw.

3. A nail-matrix trephine as claimed in claim 1, wherein said alignment means on said hooked nail engaging member comprises a surface of said hooked nail engaging member.

4. A nail-matrix trephine as claimed in claim 1, wherein said trephine cutter means comprises a screw having a cutting surface at one end thereof.

5. A nail-matrix trephine adapted to be attached to nail plate of a toe or finger for removing unwanted nail-matrix cells, including a clamping head comprising a hooked nail engaging member, a screw mounted on said clamping head co-operating with said hooked nail engaging member to firmly attach said clamping head to said nail plate, and alignment means on said hooked nail engaging member for aligning said clamping head on said nail plate, a guide head supporting and guiding a trephine cutter means mounted therein, and guide rails and an adjustable means interconnecting said clamping head and said guide head, wherein upon clamping and aligning said clamping head to said nail plate the position of said guide head is adjusted so that when said trephine cutter means is advanced a selected portion of the nail-matrix cells is removed.

6. A nail-matrix trephine adapted to be attached to a nail plate of a toe or finger for removing unwanted nail matrix cells, including a clamping head comprising a hooked nail engaging member, a screw mounted on said clamping head which co-operates with said hooked nail engaging member to firmly attach said clamping head to said nail plate, and clamp alignment means on said hooked nail engaging member for aligning said clamping head on said nail plate, a guide head supporting and guiding a trephine cutter means mounted thereon, and guide rails and a screw interconnecting said clamping head and said guide head, wherein upon clamping and aligning said clamping head to said nail plate the position of said guide head is adjusted so that when said trephine cutter means is advanced a selected portion of the nail-matrix cells is removed.

* * * * *